United States Patent [19]

Castro Pineiro et al.

[11] Patent Number: 5,510,359
[45] Date of Patent: Apr. 23, 1996

[54] HETEROAROMATIC 5-HYDROXYTRYPTAMINE RECEPTOR AGONISTS

[75] Inventors: Jose L. Castro Pineiro, Harlow; Victor G. Matassa, Furneux Pelham, both of United Kingdom

[73] Assignee: Merck Sharp & Dohme Ltd., Hoddesdon Hertfordshire, England

[21] Appl. No.: 318,610

[22] PCT Filed: Apr. 14, 1993

[86] PCT No.: PCT/GB93/00789

§ 371 Date: Oct. 7, 1994

§ 102(e) Date: Oct. 7, 1994

[87] PCT Pub. No.: WO93/21182

PCT Pub. Date: Oct. 28, 1993

[30] Foreign Application Priority Data

Apr. 16, 1992 [GB] United Kingdom ............... 9208463

[51] Int. Cl.⁶ .................. C07D 417/12; A61K 31/42
[52] U.S. Cl. .................. 514/361; 514/363; 548/128; 548/138
[58] Field of Search ............... 514/363, 361, 514/128; 548/138

[56] References Cited

U.S. PATENT DOCUMENTS

| | | |
|---|---|---|
| 4,785,016 | 11/1988 | Evans et al. . |
| 5,140,034 | 8/1993 | Baker ........................ 514/364 |
| 5,208,248 | 5/1993 | Baker ........................ 514/364 |
| 5,298,520 | 3/1994 | Baker et al. ............... 514/383 |

FOREIGN PATENT DOCUMENTS

| | | |
|---|---|---|
| 0225726A1 | 6/1987 | European Pat. Off. . |
| 0313397A1 | 4/1989 | European Pat. Off. . |
| 0328200A1 | 8/1989 | European Pat. Off. . |
| 0438230A2 | 7/1991 | European Pat. Off. . |
| 0494774A1 | 7/1992 | European Pat. Off. . |
| 0497512A2 | 8/1992 | European Pat. Off. . |
| WO 91/18897 | 12/1991 | WIPO . |

*Primary Examiner*—Robert Gerstl
*Attorney, Agent, or Firm*—Robert J. North; Melvin Winokur

[57] ABSTRACT

A class of substituted five-membered heteroaromatic compounds possessing an imino spacer group are selective agonists of 5-HT$_1$-like receptors and are therefore useful in the treatment of clinical conditions, in particular migraine and associated disorders, for which a selective agonist of these receptors is indicated.

5 Claims, No Drawings

HETEROAROMATIC 5-HYDROXYTRYPTAMINE RECEPTOR AGONISTS

This application is a 371 of PCT/GB93/00789 dated Apr. 14, 1993.

The present invention relates to a class of substituted five-membered heteroaromatic compounds possessing an imino spacer group. These compounds act on 5-hydroxytryptamine (5-HT) receptors, being selective agonists of so-called "5-HT$_1$-like" receptors. They are therefore useful in the treatment of clinical conditions for which a selective agonist of these receptors is indicated.

5-HT$_1$-like receptor agonists which exhibit selective vasoconstrictor activity have recently been described as being of use in the treatment of migraine (see, for example, A. Doenicke et al., The Lancet, 1988, Vol. 1, 1309–11). The compounds of the present invention, being selective 5-HT$_1$-like receptor agonists, are accordingly of particular use in the treatment of migraine and associated conditions, e.g. cluster headache, chronic paroxysmal hemicrania, headache associated with vascular disorders, tension headache and paediatric migraine.

The present invention provides a compound of formula I, or a salt or prodrug thereof:

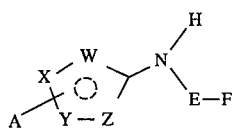

wherein the broken circle represents two non-adjacent double bonds in any position in the five-membered ring;

W, X, Y and Z independently represent oxygen, sulphur, nitrogen or carbon, provided that one of W, X, Y and Z represents oxygen or sulphur and at least one of W, X, Y and Z represents carbon;

A represents hydrogen, hydrocarbon, a heterocyclic group, halogen, cyano, trifluoromethyl, —OR$^x$, —SR$^x$, —NR$^x$R$^y$, —NR$^x$COR$^y$, —NR$^x$CO$_2$R$^y$, —NR$^x$SO$_2$R$^y$, or —NR$^z$CTNR$^x$R$^y$;

E represents a bond or a straight or branched alkylene chain containing from 1 to 4 carbon atoms;

F represents a group of formula

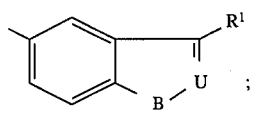

U represents nitrogen or C—R$^2$;
B represents oxygen, sulphur or N—R$^3$;
R$^1$ represents —CH$_2$·CHR$^4$·NR$^6$R$^7$ or a group of formula

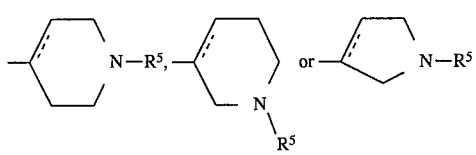

in which the broken line represents an optional chemical bond;

R$^2$, R$^3$, R$^4$, R$^5$, R$^6$ and R$^7$ independently represent hydrogen or C$_{1-6}$ alkyl;

R$^x$ and R$^y$ independently represent hydrogen, hydrocarbon or a heterocyclic group, or R$^x$ and R$^y$ together represent a C$_{2-6}$ alkylene group;

R$^z$ represents hydrogen, hydrocarbon or a heterocyclic group;

T represents oxygen, sulphur or a group of formula =N.G; and

G represents hydrocarbon, a heterocyclic group or an electron-withdrawing group.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl (C$_{1-6}$) alkyl, aryl and aryl (C$_{1-6}$) alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

A particular aryl group is phenyl.

Particular aryl(C$_{1-6}$)alkyl groups include benzyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl(C$_{1-6}$)alkyl groups include pyridylmethyl and pyrazinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl ($C_{1-6}$) alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkyl sulphonyl, aryl sulphonyl, $NR^vR^w$, —$NR^vCOR^w$, —$NR^vCO_2R^w$, —$NR^vSO_2R^w$, —$CH_2NR^vSO_2R^w$, —NHCONR$^vR^w$, —CONR$^{vRw}$, —$SO_2NR^vR^w$ and —$CH_2SO_2NR^vR^w$, in which $R^v$ and $R^w$ independently represent hydrogen, $C_{1-6}$ alkyl, aryl or aryl($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

When the group G represents an electron-withdrawing group, this group is suitably cyano, nitro, —COR$^x$, —CO$_2R^x$ or —SO$_2R^x$, in which $R^x$ is as defined above.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs" ed. H Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

The five-membered heteroaromatic ring in formula I containing the substituents W to Z may be, for example, a furan, thiophene, oxazole, thiazole, isoxazole, isothiazole, oxadiazole or thiadiazole ring, in particular a 1,2,4-oxadiazole, 1,3,4-oxadiazole, 1,2,4-thiadiazole, 1,3,4-thiadiazole, 1,3-oxazole or 1,3-thiazole ring. Preferably the ring is a 1,2,4-oxadiazole, 1,2,4-thiadiazole or 1,3,4-thiadiazole ring.

The alkylene chain E may be, for example, methylene, ethylene, 1-methylethylene, propylene or 2-methylpropylene. Alternatively, the group E may represent a single bond such that the group F in formula I is attached directly to the —NH— moiety, which in turn is connected to the five-membered heteroaromatic ring.

The group F is suitably an indole, benzofuran or benzthiophene moiety of formula FA, or an indazole moiety of formula FB:

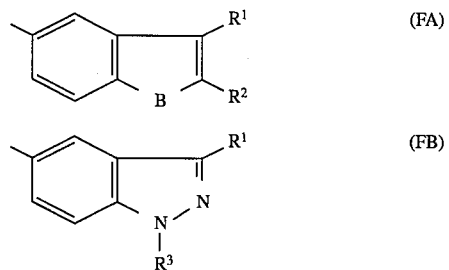

wherein B, , $R^1$ $R^2$ and $R^3$ are as defined above. Preferably, the group F represents an indole moiety of structure FC:

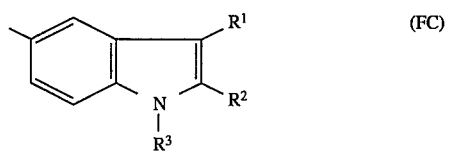

wherein $R^1$ $R^2$ and $R^3$ are as defined above, in particular wherein $R^2$ and $R^3$ are both hydrogen.

Suitable values for the group A include $C_{1-6}$ alkyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy or $C_{1-6}$ alkylthio, any of which groups may be optionally substituted; and hydrogen, halogen, cyano, trifluoromethyl or —$NR^xR^y$, in which $R^x$ and $R^y$ are as defined above. Examples of optional substituents on the group A suitably include trifluoromethyl, $C_{1-6}$ alkoxy, $C_{2-6}$ alkoxycarbonyl, $C_{2-6}$ alkylcarbonyl, $C_{2-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di(Cl6)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of A include hydrogen, methyl, methoxymethyl, aminomethyl, dimethylaminomethyl, acetylaminomethyl, benzoylaminomethyl, t-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethYl, ethoxycarbonylaminoethyl, t-butoxycarbonylaminoethyl, methylsulphonylaminoethyl, aminocarbonylaminoethyl, methylaminocarbonylaminoethYl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethylphenyl, aminosulphonylmethylphenYl, methylaminosulphonylmethylphenyl, dimethylaminosulphonylmethylphenyl, benzyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, pyridylmethyl, methoxypyridylmethyl, amino, methylamino, benzylamino, dimethylamino, t-butoxycarbonylaminoethylamino and methylsulphonylaminoethylamino.

Preferred values of A include hydrogen, methyl, ethyl, benzyl and amino, especially methyl.

Representative values of $R^1$ include aminoethyl, N-methylaminoethyl, N,N-dimethylaminoethyl, 4-piperidyl, 1-methyl-4-piperidyl, 3-pyrrolidinyl and 1-methyl-3-pyrrolidinyl.

Preferred values for the groups $R^2$ to $R^7$ are hydrogen and methyl.

A particular sub-class of compounds according to the invention is represented by the compounds of formula IIA, and salts and prodrugs thereof:

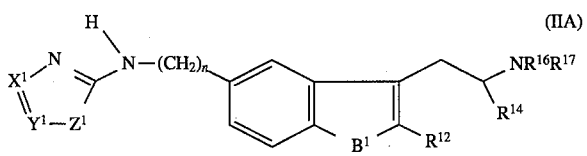

wherein
one of $X^1$ and $Y^1$ represents nitrogen and the other represents $A^1$–C;

$Z^1$ represents oxygen or sulphur;

n is zero, 1, 2 or 3;

$B^1$ represents oxygen, sulphur or N—$R^{13}$;

$A^1$ represents $C_{1-6}$ alkyl, $C_{1-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, $C_{1-6}$ alkylamino or di($C_{1-6}$)alkylamino, any of which groups may be optionally substituted; or hydrogen, halogen, cyano, trifluoromethyl or amino; and $R^{12}$, $R^{13}$, $R^{14}$, $R^{16}$ and $R^{17}$ independently represent hydrogen or $C_{1-6}$ alkyl.

Examples of optional substituents on the group $A^1$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of $A^1$ with respect to formula IIA include hydrogen, methyl, ethyl, benzyl and amino, especially methyl.

Preferably, $R^{12}$, $R^{13}$ and $R^{14}$ each represents hydrogen. Preferred values of $R^{16}$ and $R^{17}$ with respect to formula IIA include hydrogen and methyl.

Specific compounds within the scope of the present invention include: 3-(2-aminoethyl)-5-[(3-methyl-1,2,4-thiadiazol-5yl)aminomethyl] -1H-indole; 3-[2-(dimethylamino)ethyl]-5-[(5-methyl-1,3,4-thiadiazol- 2-yl)aminomethyl]-1H-indole; and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to this invention wherein the group F is an indole moiety of structure FC as defined above may be prepared by a process which comprises reacting a compound of formula III:

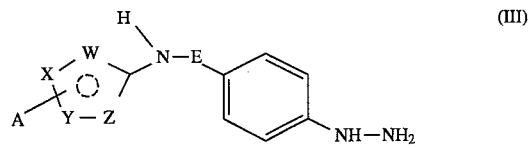

wherein W, X, Y, Z, A and E are as defined above; with a compound of formula IV or a carbonyl-protected form thereof:

wherein $R^2$ is as defined above and $R^{11}$ corresponds to the group $R^1$ as defined above or represents a group of formula —$CH_2 \cdot CHR^4 D^1$, in which $R^4$ is as defined above and $D^1$ represents a readily displaceable group; followed, where required, by N-alkylation by standard methods to introduce the moiety $R^3$.

Suitable carbonyl-protected forms of the compounds of formula IV include the dimethyl acetal or ketal derivatives.

The readily displaceable group $D^1$ in the compounds of formula IV suitably represents a halogen atom, preferably chlorine. When the moiety $R^{11}$ in the compounds of formula IV is a group of formula —$CH_2 \cdot CHR^4 D^1$, the substituent $D^1$ is displaced in situ under the prevailing reaction conditions to afford a final product of formula I wherein $R^1$ represents a group of formula —$CH_2 \cdot CHR^4 \cdot NH_2$. The terminal amino group can subsequently, if desired, be further elaborated using techniques known from the art to give a compound of formula I wherein $R^1$ represents the required group of formula $-CH_2 \cdot CHR^4 \cdot NR^6R^7$.

The reaction of compounds III and IV may be carried out in a single step (Fischer indole synthesis) or by an initial non-cyclising step at a lower temperature to give a compound of formula V:

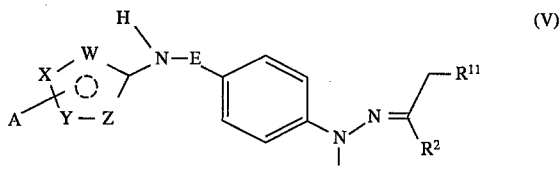

wherein W, X, Y, Z, A, E, $R^2$ and $R^{11}$ are as defined above; followed by cyclisation using a suitable reagent, such as a polyphosphate ester.

The hydrazines of formula III may be prepared from the corresponding anilines of formula VI:

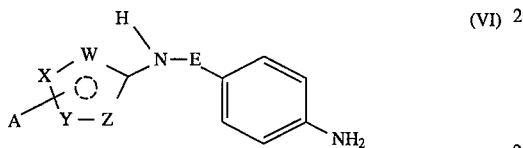

wherein W, X, Y, Z, A and E are as defined above; by diazotisation followed by reduction. Diazotisation is typically carried out using sodium nitrite/conc. HCl and the resulting diazo product reduced in situ using, for example, tin(II) chloride/conc. HCl, sodium sulphite/conc. HCl, or sodium sulphite/conc. $H_2SO_4$.

The anilines of formula VI may be prepared by reduction of the corresponding nitro compounds of formula VII:

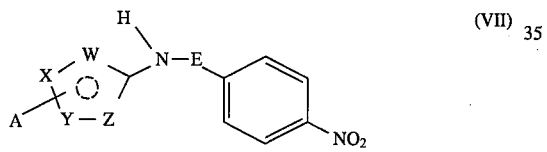

wherein W, X, Y, Z, A and E are as defined above; typically by transfer hydrogenation using a hydrogenation catalyst such as palladium on charcoal in the presence of a hydrogen donor such as ammonium formate, or alternatively by conventional catalytic hydrogenation or using tin(II) chloride.

The nitro compounds of formula VII may be prepared by a variety of methods which will be readily apparent to those skilled in the art. One such method involves reacting an amino compound of formula VIII with a compound of formula IX:

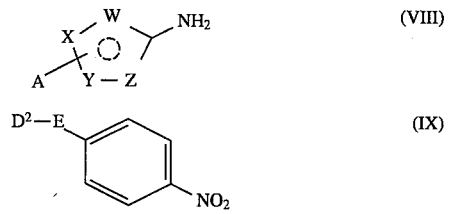

wherein W, X, Y, Z, A and E are as defined above, and $D^2$ represents a readily displaceable group.

The reaction is conveniently carried out in the presence of sodium hydride using N,N-dimethylformamide as solvent.

The readily displaceable group $D^2$ in the compounds of formula IX is suitably a halogen atom, preferably bromine; except when the moiety $D^2$ is attached directly to the aromatic ring, i.e. when E represents a bond, in which case $D^2$ is preferably fluorine.

The compounds according to the invention wherein the group F is an indazole moiety of structure FB as defined above may be prepared by a process which comprises the cyclisation of a compound of formula X:

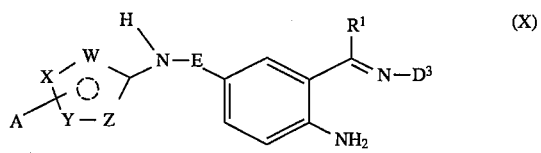

wherein W, X, Y, Z, A, E and $R^1$ are as defined above; and $D^3$ represents a readily displaceable group; followed, where required, by N-alkylation by standard methods to introduce the moiety $R^3$.

The cyclisation of compound X is conveniently achieved in a suitable organic solvent at an elevated temperature, for example in a mixture of m-xylene and 2,6-lutidine at a temperature in the region of 140° C.

The readily displaceable group $D^3$ in the compounds of formula X suitably represents a $C_{1-4}$ alkanoyloxy group, preferably acetoxy. Where $D^3$ in the desired compound of formula X represents acetoxy, this compound may be conveniently prepared by treating a carbonyl compound of formula XI:

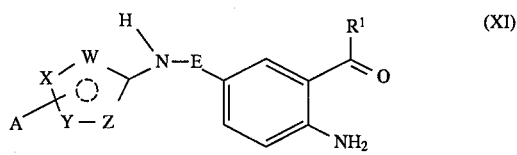

wherein W, X, Y, Z, A, E and $R^1$ are as defined above; or a protected derivative thereof; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivative of the intermediate of formula XI may be conveniently prepared by ozonolysis of an indole derivative of formula XII:

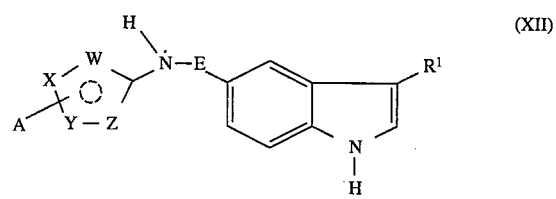

wherein W, X, Y, Z, A, E and $R^1$ are as defined above; followed by a reductive work-up, advantageously using dimethylsulphide.

The indole derivative of formula XII may be prepared by methods analogous to those described in the accompanying Examples, or by procedures well known from the art.

In an alternative process, the compounds according to the invention may be prepared by a method which comprises reacting a compound of formula XIII:

wherein W, X, Y, Z and A are as defined above, and L represents a suitable leaving group; with a compound of formula $H_2N$-E-F, in which E and F are as defined above.

The reaction is conveniently carried out in the presence of an organic base such as diisopropylamine or diisopropylethylamine, in a suitable solvent such as 2-ethoxyethanol or tetrahydrofuran, advantageously at the reflux temperature of the reaction mixture.

The leaving group L suitably represents halogen, e.g. chlorine, or a nitro group.

In further process, the compounds according to the invention in which E is other than a chemical bond may be prepared by reacting a compound of formula OHC—$E^1$—F, wherein F is as previously defined and $E^1$ represents a bond or a straight or branched alkylene chain containing from 1 to 3 carbon atoms; with a compound of formula VIII as defined above; followed by treatment with a reducing agent. The resulting product is a compound of formula I as defined above in which the group E is represented by a moiety of formula —$CH_2E^1$—.

The above reaction is advantageously carried out in two stages. In the first stage, the reagents are suitably heated together under reflux, with removal of water, in a suitable solvent such as toluene, optionally in the presence of a protic solvent such as ethanol. Removal of water is conveniently effected by standard means such as by the utilisation of 3A molecular sieves, or in a Dean-Stark apparatus. In the second stage, the product obtained from the first stage is treated, preferably crude, with a reducing agent, advantageously in an alcoholic solvent such as methanol. A preferred reducing agent for use in this process is sodium borohydride.

In a yet further process, the compounds according to the invention wherein the group F is a benzofuran or benzthiophene moiety may be prepared by a method which comprises cyclising a compound of formula XIV:

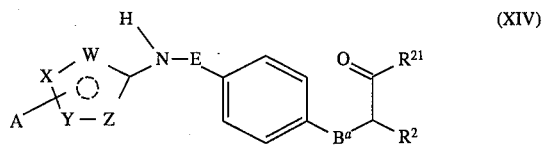

(XIV)

wherein W, X, Y, Z, A, E and $R^2$ are as defined above, $B^a$ represents oxygen or sulphur, and $R^{21}$ corresponds to the group $R^1$ as defined above or represents a precursor group thereto as discussed below; followed, where required, by conversion of the group $R^{21}$ into the desired group $R^1$ by conventional means.

The cyclisation is conveniently effected by using polyphosphoric acid or a polyphosphate ester, advantageously at an elevated temperature.

The compounds of formula XIV may be prepared by reacting a compound of formula XV with a compound of formula XVI:

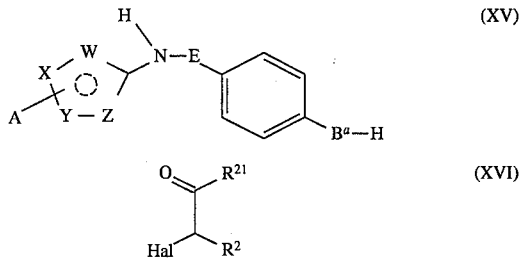

(XV)

(XVI)

wherein W, X, Y, Z, A, E, $B^a$, $R^2$ and $R^{21}$ are as defined above, and Hal represents halogen.

The reaction is conveniently effected in the presence of a base such as sodium hydroxide.

The hydroxy and mercapto derivatives of formula XV may be prepared by a variety of methods which will be readily apparent to those skilled in the art. In one such method, a compound of formula VIII as defined above is reacted with a compound of formula XVII:

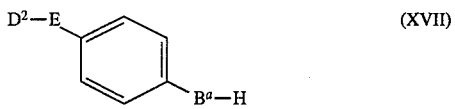

(XVII)

wherein $D^2$ E and $B^a$ are as defined above

Where they are not commercially available, the intermediates of formula IV, VIII, IX, XIII, XVI, XVII, $H_2N$—E—F and OHC—$E^1$—F referred to above may be prepared by methods analogous to those described hereinafter for the preparation of Intermediates 1 to 3; or by procedures known from the art.

It will be understood that any compound of formula I initially obtained from any of the above processes may, where appropriate, subsequently be elaborated into a further compound of formula I by techniques known from the art. In particular, a compound of formula I wherein $R^1$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide. Similarly, a compound of formula I wherein $R^1$ represents a group of formula —$CH2\cdot CHR^4\cdot NH_2$ initially obtained may be converted into a compound of formula I wherein $R^1$ represents a group of formula —$CH_2\cdot CHR^4\cdot NR^6R^7$ in which $R^6$ and $R^7$ independently represent $C_{1-6}$ alkyl, by conventional N-alkylation techniques, e.g. by treatment with the appropriate aldehyde in the presence of a reducing agent such as sodium cyanoborohydride.

Where the above-described processes for the preparation of the compounds according to the invention give rise to mixtures of stereoisomers, these isomers may be separated by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic synthesis*, John Wiley & Sons, 1991. The protecting groups may be removed at a convenient subsequent stage using methods known from the art.

Alternatively, certain of the functional groups on the desired products may be carried through the reaction sequence as precursor groups, and then regenerated from these precursor groups at a late stage in the overall synthesis. For example, where $R^1$ in the desired compound of formula I represents a group of formula —$(CH_2)_2NH_2$, this group can be generated from a cyano precursor —$CH_2CN$ by reduction using, for example, borane/tetrahydrofuran. The cyano precursor may in turn be carried through the reaction sequence as a methyl group —CH$_3$, which may conveniently be converted to —CH$_2$CN by treatment with N-bromosuccinimide and benzoyl peroxide, in the presence of a bright light source, followed by reaction of the resulting bromo intermediate with sodium cyanide in dimethyl sulphoxide.

The following Examples illustrate the preparation of compounds according to the invention.

The ability of test compounds to bind to 5-HT$_1$-like receptors was measured in membranes prepared from pig caudate using the procedure described in *J. Neurosci.*, 1987, 7, 894. Binding was determined using 2 nM 5-hydroxytryptamine creatinine sulphate, 5-[1,2-$^3$H(N)] as a radioligand. Cyanopindolol (100 nM) and mesulergine (100 nM) were included in the assay to block out 5-HT$_{1A}$ and 5-HT$_{1C}$ binding sites respectively. The concentration of the compounds of the accompanying Examples required to displace 50% of the specific binding (IC$_{50}$) is below 1 μM in each case.

The activity of test compounds as agonists of the 5-HT$_1$-like receptor was measured in terms of their ability to mediate contraction of the saphenous vein of New Zealand White rabbits, using the procedure described in *Arch. Pharm.*, 1990, 342, Ill. Agonist potencies were calculated as —log$_{10}$EC$_{50}$ (pEC$_{50}$) values, from plots of percentage 5-HT (1 μm) response against the concentration of the agonist. The compounds of the accompanying Examples were found to possess pEC$_{50}$ values in this assay of not less than 5.0 in each case.

INTERMEDIATE 1

3-[2-(Dimethylamino)ethyl]-1H-indole-5-carboxaldehyde 1,4-Cyanophenylhydrazine, Hydrochloride To a cooled (−15° C.) and stirred suspension of 4-aminobenzonitrile (50g, 423mmol) in concentrated hydrochloric acid (550ml) was added dropwise a solution of sodium nitrite (31.5g, 457mmol) in water (200ml) at such a rate as to maintain the temperature below −10° C. After the addition was finished, the reaction mixture was quickly filtered to remove solids and the flitrate was added portionwise to a cooled (−20° C.) and stirred solution of tin (II) chloride dihydrate (477g, 2.1mol) in concentrated hydrochloric acid (370m1) at such a rate as to maintain the temperature below −10° C. After further 15 minutes at −10° C. to 0° C., the white precipitate was collected by filtration, washed with diethyl ether (4×250ml) and dried to give 56 g (78%) of the title compound; mp 235+−237° C. (ethanol-water 1:1); δ$_H$ (250MHz, DMSO-d$_6$) 10.50 (3H, br s, —N$^+$H$_3$), 9.10 (1H, br s, —NH—), 7.71 (2H, d, J=8.8Hz, Ar-H), 7.03 (2H, d, J=8.8 Hz, Ar-H); m/z (CI) 132 (M$^+$−1).

2.3-( 2-Aminoethyl)-5-cyano-1H-indole, Hydrochloride

To a stirred suspension of 4-cyanophenylhydrazine hydrochloride (50 g) in a mixture of ethanol and water (5:1; 21) was added 4-chlorobutanal dimethylacetal (45 g) and the resulting mixture was refluxed for 18 hours. Solvents were removed under vacuum and the residue was azeotroped with toluene to give a brown solid. Crystallisation of this crude material from methanol (150 ml) gave 23 g (35%) of the title compound as a yellow solid; mp 270°−274° C.; δ$_H$ (250 MHz, DMSO-d$_6$) 11.60 (1H, br s, indole N-H), 8.17 (1H, d, J=1.1 Hz, Ar-H), 7.97 (3H, br s, —N$^{+H}$$_3$), 7.54 (1H, d, J=8.5 Hz, Ar-H), 7.46 (1H, s, Ar-H), 7.44 (1H, dd, J=8.5 and 1.1 Hz, Ar-H), 3.05 (4H, br s, —CH$_2$CH$_2$N—); m/z (CI) 184 (M$^+$1).

3. 5-Cyano-3-f2-(dimethylamino)ethyl]-1H-indole

To a cooled (5° C.) and stirred solution of sodium methoxide in anhydrous methanol (from 1.75 g of sodium metal in 400ml of methanol) was added 3-(2-aminoethyl)-5-cyano-1H-indole hydrochloride (18.6 g) and the mixture was stirred for a further 5 minutes before sodium cyanoborohydride (7.2 g) and glacial acetic acid (10.4 ml) were added. A solution of formaldehyde (37% aqueous solution; 19.9ml) in methanol (50 ml) was added dropwise over 30 minutes and the mixture was then allowed to warm to room temperature and stirred for a further 15 minutes. Solvents were removed under vacuum and the residue was diluted with saturated aqueous potassium carbonate (400 ml) and products were extracted with ethyl acetate (3×400 ml). The combined organic extracts were dried (MgSO$_4$) and concentrated. Flash chromatography of the residue ( silica gel, dichloromethane-methanol-ammonia, 40:8:1) gave 10.5 g of the title compound as a pale yellow solid; δ$_H$ (250 MHz, CDCl$_3$) 8.60 (1H, br s, indole N-H), 7.94 (1H, d, J=1.5 Hz, Ar-H), 7.39 (1H, dd, J=8.5 and 1.5 Hz, Ar-H), 7.13 (1H, br d, Ar-H), 2.94 (2H, m, —CH$_2$—), 2.66 (2H, m, —CH$_2$—), 2.35 (6H, s, —NMe$_2$); m/z (FAII) 212 (M$^+$−1).

4. 3-[2-(Dimethylamino)ethyl]- 1H-indole-5-carboxaldehyde.

To a solution of the product from step 3 (10.5g) in a mixture of water, acetic acid and pyridine (1:1:2; 600ml) were added sodium hypophosphite hydrate (20.6g) and Raney nickel (50% slurry in water; 5.0 g) and the mixture was stirred at 40° C. for 24 hours under nitrogen. After being cooled to room temperature, the mixture was filtered and solvents were removed under vacuum. The remaining residue was dissolved in water (300 ml), basified to pH 10 with solid potassium carbonate and products were extracted with dichloromethane (3×300ml), dried (Na$_2$SO$_4$) and concentrated to give the title compound (8.6 g) as a pale yellow solid; δ$_H$ (360 MHz, CDCl$_3$) 10.04 (1H, s, —CHO), 8.6 (1H, br s, indole N-H), 8.15 (1H, br s, Ar-H), 7.73 (1H, dd, J=8.5 and 1.4Hz, Ar-H), 7.38 (1H, d, J=8.5 Hz, Ar-H), 7.11 (1H, br s, Ar-H), 3.00 (2H, t, J=8.2 Hz, —CH$_2$—), 2.69 (2H, t, J=8.2 Hz, —CH$_2$—), 2.36 (6H, s, —NMe$_2$).

INTERMEDIATE 2

1-tert-Butyloxycarbonyl-3-[2-(dimethylamino)ethyl]-indol- 5-carboxaldehyde

To a solution of Intermediate I (8.4 g, 39 mmol) in anhydrous acetonitrile ( 150 ml ) was added di-tert-butyldicarbonate ( 12.7 g, 58 mmol) followed by 4-dimethylaminopyridine (476 mg, 3.9 mmol) and the resulting mixture was stirred for two hours at room temperature under nitrogen. Solvents were removed under vacuum and the residue was purified by flash chromatography (silica gel, dichloromethane-methanol-ammonia, 90:10:1) to give 10.5 g (83%) of the title compound as a viscous oil; δ$_H$ (250 MHz, CDCl$_3$) 10.08 (1H, s, —CHO), 8.25 (1H, d, J=8.6Hz, Ar-H), 8.07 (1H, d, J=1.5 Hz, Ar-H), 7.83 (1H, dd, J=8.6 and 1.5 Hz, Ar-H), 7.50 (1H, s, Ar-H), 2.93 (2H, m, —CH$_2$—), 2.67 (2H, m, -CH2-), 2.34 (6H, s, —NMe$_2$), 1.68 (9H, s, t-Bu).

INTERMEDIATE 3

5-Aminomethyl-3[2-(N; tert-butyloxycarbonylamino)ethyl] -1H-indole 1. 3-[2-(N-tert-Butyloxycarbonylamino)ethyl]-5-cyano-1H-indole To a cooled (−20° C.) and stirred suspension of 3-(2-aminoethyl)-5-cyano-1H-indole hydrochloride (15 g, 68 mmol) in anhydrous dichloromethane (500 ml) and anhydrous triethylamine (13.7 g, 136 mmol) was added di-tert-butyldicarbonate (19.3 g, 88mmol). After being stirred at −20° C. for 0.5 hours and at room temperature for 1.5 hours, the reaction mixture was diluted with dichloromethane (300 ml), (Na$_2$SO$_4$) and concentrated. Flash chromatography of the washed with 2N hydrochloric add (300 ml), brine (300 ml), dried residue (silica gel, dichloromethane-methanol, 96:4) gave 11.3 g of the title compound as a white solid; mp 132°–134° C. (hexane-ethyl acetate); $\delta_H$ (250 MHz, CDCl$_3$) 8.42 (1H, br s, indole N-H), 7.93 (1H, s, Ar-H), 7.41 (2H, s, Ar-H), 7.12 (1H, d, J=2.2 Hz, Ar-H), 4.71 (1H, br s, —NH—), 3.44 (2H, q, J=6.9 Hz, —CH$_2$NH—), 2.94 (2H, t, J=6.9 Hz, Ar—CH$_2$—), 1.45 (9H, s, t-Bu); m/z (CI) 286 (M$^+$+1).

2. 5-Aminomethyl-3-[2-(N-tert-butyloxVcarbonylamino) ethyl-1H-indole

A solution of the product from the previous step (11.3 g) in a mixture of absolute ethanol (750 ml) and chloroform (22 ml) was hydrogenated at 50 psi over platinum (IV) oxide (1 g) for 28 hours. The catalyst was removed by filtration and solvents were removed under vacuum. Flash chromatography of the residue (silica gel, dichloromethane-methanol-ammonia, 90:10:1) gave 9.5 g (82%) of the title compound as a white solid; mp 147°–149° C. ethyl acetate-diethyl ether); $\delta_H$ (360 MHz, CDCl$_3$) 8.04 (1H, br s, indole N-H), 7.52 (1H, s, Ar-H), 7.33 (1H, d, J=8.4 Hz, Ar-H), 7.16 (1H, d, J=8.4 Hz, Ar-H), 7.03 (1H, s, Ar-H), 4.61 (1H, br s, —NHBOC), 3.96 (2H, s, Ar-CH$_2$NH$_2$), 3.45 (2H, br q, —CH$_2$NHBOC), 2.95 (2H, t, J=6.8 Hz, Ar—CH$_2$—), 1.43 (9H, s, t-Bu); m/z (CI) 288 (M$^+$−1).

EXAMPLE 1

3-( 2-Aminoethyl )-5-[(3-methyl-1,2,4-thiadiazol-5-yl]amino methyl]-1H-indole, Oxalate 1. 3-[2-(tert-Butyloxycarbonylamino)ethyl]-5-[(3-methyl-1.2.4- thiadiazol-5-yl)aminomethyl]-1H-indole To a stirred solution of Intermediate 3 (500 mg, 1.72 mmol) in anhydrous tetrahydrofuran (8 ml) and anhydrous diisopropylethylamine (0.30 ml) was added 5-chloro-3-methyl-1,2,4-thiadiazole (403mg, 3.0 mmol) and the mixture was refluxed for 24 hours under nitrogen. After being dried (Na$_2$SO$_4$) and concentrated. Flash chromatography of the cooled to room temperature, water (10 ml) was added and products were extracted with dichloromethane (3×30 ml), then residue (silica gel, hexane-ethyl acetate, 40:60) gave 263 mg (43%) of the title compound as a white solid; $\delta_H$(250 MHz, CDCl$_3$) 8.17 (1H, br s, indole N-H), 7.56 (1H, s, Ar-H), 7.35 (1H, d, J= 8.3 Hz, Ar-H), 7.17 (1H, dd, J=1.3 and 1.4 Hz, Ar-H), 7.06 (1H, d, J=2.2 Hz, Ar-H), 6.35 (1H, br s, —NH—), 4.62 (1H, br s, —NHBOC), 4.51 (2H, d, J=4.0 Hz, Ar—CH$_2$—N), 3.42 (2H, m, —CH$_2$NHBOC), 2.93 (2H, t, J=6.9 Hz, Ar—CH$_2$—), 2.38 (3H, s, —Me), 1.43 (9H, s, t-Bu); m/z (FAB$^-$) 386 (M$^+$1).

2. 3-(2-Aminoethyl)-5-[(3-methyl-1.2.4-thiadiazol-5-yl) aminomethvl]-1H-indole. Oxalate A solution of the product from the previous step (105 mg) in anhydrous dichloromethane (2 ml) and trifiuoroacetic acid (0.6 ml) was stirred under nitrogen for I hour. Solvents were removed under vacuum and the remaining residue was purified by flash chromatography (silica gel, dichloromethane-methanol-ammonia, 85:15:1) to give 75 mg of the title compound free base as a white solid. The oxalate salt was prepared; mp 121°–123° C. (methanol-diethyl ether); $\delta_H$ (250 MHz, DMSO-d$_6$) 10.98 (1H, s, indole N-H), 8.76 (1H, br s, —NH—), 7.52 (1H, s, Ar-H), 7.35 (1H, d, J=8.3 Hz, Ar-H), 7.24 (1H, d, J=2.1 Hz, Ar-H), 7.09 (1H, dd, J=8.3 and 1.5 Hz, Ar-H), 4.52 (2H, s, Ar—CH$_2$—N), 3.06 (2H, m, —CH$_2$—), 2.98 (2H, m, —CH$_2$—), 2.25 (6H, s, —NMe$_2$); m/z (CI) 288 (M$^+$+1). (Found: C, 50.68; H, 5.08; N, 17.69. C$_{14}$H$_{17}$N$_5$S×1.1 C$_2$H$_2$O$_4$×0.1 C$_4$H$_{10}$O requires: C, 50.63; H, 5.17; N, 17.78%).

EXAMPLE 2

8-[2-(Dimethylamino)ethyl]-5-[(5-methyl-1,3,4-thiadiazol-2 -y]) aminomethyl]-1H-indole. Oxalate 1. 1-tert-Butyloxycarbonyl-3-[2-dimethylamino)ethyl-5-[(5-methyl- 1,3,4-thiadiazol-2-yl)aminomethyl]-indole A mixture of Intermediate 2 (225 mg, 0.71mmol), 2-amino-5-methyl-1,3,4-thiadiazole (123 mg, 1.07mmol) and p-toluenesulfonic acid (12 mg) in anhydrous toluene (10 ml) was refluxed, using a Dean-Stark trap, for 4.5 hours under nitrogen. The toluene was removed under vacuum and the residue was dissolved in anhydrous methanol (10 ml) and treated with solid sodium borohydride (400 mg) over 1 hour. After further 15 hours of stirring at room temperature, the solvent was removed under vacuum and the residue dissolved in 2N hydrochloric acid (10 ml) and then basified with 2N sodium hydroxide. Products were extracted with ethyl acetate (4×40ml), washed with brine (1× 15 ml), dried (MgSO$_4$) and concentrated. Flash chromatography of the residue (silica gel, dichloromethane-methanol-3mmonia, 92:8:0.8; and dichloromethane-methanol, 88:12 to dichloromethane-methanol-ammonia, 90:10:1) gave 165 mg (56%) of the title compound as a colourless thick oil; $\delta_H$ (250 MHz, CDCl$_3$) 8.08 (1H, d, J=8.3 Hz, Ar-H), 7.51 (1H, d, J=1.6 Hz, Ar-H), 7.41 (1H, s, Ar-H), 7.30 (1H, dd, J=8.3 and 1.6 Hz, Ar-H), 5.48 (1H, br s, —NH—), 4.60 (2H, s, Ar-CH$_2$-N), 2.85 (2H, m, —CH$_2$—), 2.61 (2H, m, —CH$_2$—), 2.56 (3H, s, —Me), 2.33 (6H, s, —NMe$_2$), 1.66 (9H, s, t-Bu); m/z (CI) 416 (M$^+$+1).

2. 3-[2,(Dimethylamino )ethyl]-5-(5-methyl-1.3.4-thiadiazol- 2- yl)aminomethyl)-1H-indole. Oxalate A solution of the product from the previous step (160 mg) in a mixture of dichloromethane (16m]), trifiuoroacetic acid (4 ml) and water (0.5ml) was allowed to stand at room temperature for 2.5 hours under nitrogen. Solvents were removed under vacuum and the residue was azeotroped with methanol (1×10 ml) before it was dissolved in saturated aqueous potassium carbonate (10 ml) and products were extracted with ethyl acetate (2×40 ml). The combined organic solutions were washed with brine (1× 10 ml), dried (MgSO$_4$) and concentrated. Flash chromatography of the residue. (silica gel, dichloromethane-methanol-ammonia, 85:15:1.5) gave 95 mg (78%) of the title compound free base as a colourless thick oil. The oxalate salt was prepared and recrystallised from a mixture of ethanol and methanol; mp 207°–209° C.; $\delta_H$ (360 MHz, DMSO-d$_6$) 10.95 (1H, s, indole N-H), 7.96 (1H, br s, —NH—), 7.57 (1H, s, Ar-H), 7.33 (1H, d, J=8.3 Hz, Ar-H), 7.23 (1H, s, Ar-H), 7.11 (1H, d, J=8.3 Hz, Ar-H), 4.49 (2H, s, Ar-CH$_2$-N), 3.26 (2H, m, —CH$_2$—), 3.05 (2H, m, —CH$_2$—), 2.80 (6H, s, —NMe2), 2.43 (3H, s, —Me); m/z (CI) 315 (M$^+$). (Found: C, 51.57; H, 5.63; N, 16.35. C$_6$H$_{21}$N$_5$S×1.3 C$_2$H$_2$O$_4$ requires: C, 51.66; H, 5.50; N, 16.19%).

EXAMPLE 3

Tablet Preparation

Tablets containing 1.0, 2.0, 25.0, 26.0, 50.0 and 100.0 mg, respectively of the following compounds are prepared as illustrated below:

3-( 2-Aminoethyl )-5-[(3-methyl-1,2,4-thiadiazol-5-yl)amino methyl]-1H-indole. Oxalate 3-[ 2-(Dimethylamino )ethyl]-5-[ ( 5-methyl- 1,3,4-thiadiazol-2 -yl) aminomethyl]-1H-indole. Oxalate

| TABLE FOR DOSES CONTAINING FROM 1–25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

We claim:

1. A compound of formula I, or a pharmaceutically acceptable salt or prodrug thereof:

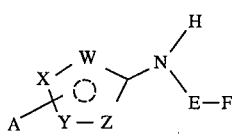

wherein the broken circle represents two non-adjacent double bonds in any position in the five-membered ring;

W, X, Y and Z independently represent oxygen, sulphur, nitrogen or carbon, provided that one of W, X, Y and Z represents oxygen or sulphur and at least one of W, X, Y and Z represents carbon;

A represents hydrogen, hydrocarbon, a heterocyclic group, halogen, cyano, trifluoromethyl, —OR$^x$, —SR$^x$, —NR$^x$R$^y$, —NR$^x$CO$_2$R$^y$, —NR$^x$CO2R$^y$, —NR$^x$SO$_2$R$^y$, or —NR$^z$CTNR$^x$R$^y$;

E represents a bond or a straight or branched alkylene chain containing from i to 4 carbon atoms;

F represents a group of formula

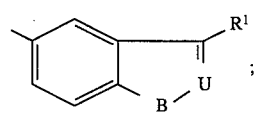

U represents nitrogen or C—R$^2$;

B represents oxygen, sulphur or N—R$^3$;

R$^1$ represents —CH$_2$·CHR$^4$·NR$^6$R$^7$ or a group of formula

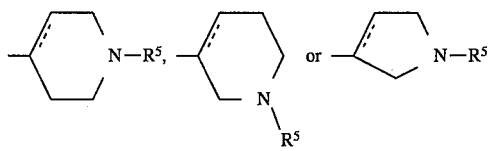

in which the broken line represents an optional chemical bond;

R$^2$, R$^3$, R$^4$, R$^5$, R$^6$ and R$^7$ independently represent hydrogen or C$_{1-6}$ alkyl;

R$^x$ and R$^y$ independently represent hydrogen, hydrocarbon or a heterocyclic group, or R$^x$ and R$^y$ together represent a C$_{2-6}$ alkylene group;

R$^z$ represents hydrogen, hydrocarbon or a heterocyclic group;

T represents oxygen, sulphur or a group of formula =N.G; and

G represents hydrocarbon, a heterocyclic group or an electron-withdrawing group.

2. A compound as claimed in claim 1 represented by formula IIA, and pharmaceutically acceptable salts and thereof:

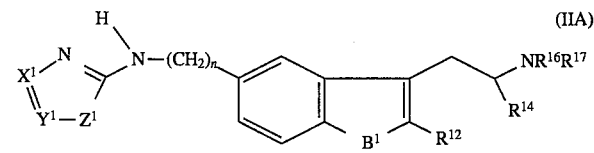

wherein one of X$^1$ and Y$^1$ represents nitrogen and the other represents A$^1$-C;

Z$^1$ represents oxygen or sulphur;

n is zero, 1, 2 or 3;

B$^1$ represents oxygen, sulphur or N-R$^{13}$;

A$^1$ represents C$_{1-6}$ alkyl, C$_{2-6}$ alkenyl, C$_{2-6}$ alkynyl, C$_{3-7}$ cycloalkyl, aryl, aryl (C$_{1-6}$) alkyl, C$_{3-7}$ heterocycloalkyl, heteroaryl, heteroaryl (C$_{1-6}$) alkyl, C$_{1-6}$ alkoxy, C$_{1-6}$ alkylthio, C$_{1-6}$ alkylamino or di(C$_{1-6}$)alkylamino, any of which groups may be optionally substituted; or hydrogen, halogen, cyano, trifluoromethyl or amino; and R$^{12}$, R$^{13}$, R$^{14}$, R$^{16}$ and R$^{17}$ independently represent hydrogen or C$_{1-6}$ alkyl.

3. A compound as claimed in claim 1 selected from:
3-(2-aminoethyl)-5-[(3-methyl-1,2,4-thiadiazol-5yl)aminomethyl] -1H-indole;
3-[2-(dimethylamino)ethyl]-5-[(5-methyl-1,3,4-thiadiazol-2-yl)aminomethyl]-1H-indole;
and pharmaceutically acceptable salts and thereof.

4. A pharmaceutical composition comprising a compound as claimed in in association with a pharmaceutically acceptable carrier or excipient.

5. A method for the treatment and/or prevention of clinical conditions for which a selective agonist of 5-HT$_1$-like receptors is indicated, which method comprises administering to a patient in need of such treatment an effective amount of a compound of formula I as defined in claim 1, or a pharmaceutically acceptable salt thereof.

* * * * *